United States Patent [19]

Ross et al.

[11] Patent Number: 5,332,572
[45] Date of Patent: Jul. 26, 1994

[54] METHOD FOR PROTECTION OF SWINE AGAINST *PLEUROPNEUMONIA*

[75] Inventors: Richard F. Ross, Ames, Iowa; Yu-Wei Chaing, St. Joseph, Mo.; Theresa F. Young, Ames, Iowa; Vicki Rapp-Gabrielson, Fargo, N. Dak.

[73] Assignee: Iowa State University Research Foundation, Ames, Iowa

[21] Appl. No.: 616,238

[22] Filed: Nov. 20, 1990

Related U.S. Application Data

[63] Continuation-in-part of Ser. No. 269,799, Nov. 10, 1988, abandoned.

[51] Int. Cl.$^5$ .................. A61K 39/102; A61K 35/74; A61K 31/715
[52] U.S. Cl. .................. 424/234.1; 424/520; 514/54
[58] Field of Search .................. 424/92, 87, 520; 435/68.1; 536/1.1, 127; 514/54

[56] References Cited

U.S. PATENT DOCUMENTS 4,789,544 12/1988 Nelson et al. .................. 424/92

FOREIGN PATENT DOCUMENTS 2197193 5/1988 United Kingdom .

OTHER PUBLICATIONS

Rapp et al., Infect. Immun., vol. 54 No. 3, Dec. 1986, pp. 751–760.
Fenwick et al., Infect. Immun., vol. 54 No. 2, Nov. 1986, pp. 575–582.
Inzana et al., Infect. Immun., vol. 56 (1988), pp. 1880–1889.
Cash et al., J. of Inf. Dis., vol. 130, No. 4, p. 325 (Oct. 1974).
Eisenstein et al. J. of Inf. Dis., vol. 150, No. 3, p. 425 (Sep. 1984).
Olander et al., Microbial Pathogenesis 1990, 8:37–45.

*Primary Examiner*—Jacqueline Stone
*Attorney, Agent, or Firm*—Tilton, Fallon, Lungmus & Chestnut

[57] ABSTRACT

The respiratory mucosa of swine are sensitized for the production of protective IgA antibodies on infection with *Actinobacillus (Haemophilus) pleuropneumoniae* by prior administration of a vaccine comprising a protease lysate of the outer membrane (OM) of *A. pleuropneumoniae* cells. The lysate contains native OM lipopolysaccharide together with a protease digest of OM protein. Preferably two doses of the vaccine are successively administered to provide protective antibodies in the respiratory mucosa prior to infection.

8 Claims, No Drawings

METHOD FOR PROTECTION OF SWINE AGAINST *PLEUROPNEUMONIA*

RELATED APPLICATION

This application is a continuation-in-part of co-ending application Ser. No. 07/269,799, filed Nov. 10, 1988 now abandoned.

FIELD OF INVENTION

The field of this invention is vaccines for increasing the resistance of swine to infection by *Actinobacillus (Haemophilus) pleuropneumoniae*.

*Actinobacillus (haemophilus) pleuropneumoniae* is the cause of a severe respiratory disease in swine that is characterized by necrotizing pneumonia with pleuritis. Infections in immunologically naive animals can be fatal, and surviving animals are stunted and frequently asymptomatic carriers. Presently used methods of controlling pleuropneumonia in pigs have been largely ineffective.

Bacterins containing antigens to the prevalent serotypes of *Actinobacillus pleuropneumoniae* (APP) have been commercially available for several years. These products consist of chemically-inactivated, oil- or aluminum-adjuvanted, whole-cell preparations. However, it has been repeatedly demonstrated both experimentally and with field usage that although vaccination with these products may reduce the clinical symptoms, pneumonia, and mortality associated with acute infection, vaccinated pigs may still become subclinically or chronically infected. Furthermore, the use of these products can be associated with systemic or local untoward reactions.

The lack of a safe effective vaccine for immunization of swine against pleuropneumonia has engendered considerable research, but the problems involved have been found to be immunologically very complex. APP exists in a number of serotypes of which serotype 5 is the most common field isolate in the United States.

The serotypes produce both cross-reacting and serotype specific antibodies. However, pigs that survive an infection with any *A. pleuropneumoniae* serotype not only develop strong serotype-specific immunity but are also resistant to reinfection by other serotypes: Nielsen, *Nord. Veterinaeromed.*, 31:407–413 (1979); and 28:337–348 (1976). Killed whole-cell bacterins do not produce corresponding immunity, serum antibody titers correlate poorly with protective immunity, and bacterins made from whole-cell cultures provide little protection: Nielsen (1979), cited above; Pijoan, et al., Abstr. Int. Pig Vet. Soc. Congr., 1982, p. 73; and Henry, et al., Abstr. Int. Pig Vet. Soc. Congr. 1982, p. 72.

Recent research has been directed toward development of subunit vaccines. The membranes of APP contain lipopolysaccharides (LPS) which have been isolated and found to produce immunological responses: Fenwick, et al. (1986), *Infect. Immun.*, 54: 575–582. Although these authors suggested a further investigation of LPS as a vaccine, no effective LPS vaccine has been reported. Capsule polysaccharide has also been investigated as a potential subunit vaccine: Inzana, et al. (1988), *Infect. Immun.*, 56:1880–1889, found that antibody to the capsule was not fully protective and is serotype specific.

Rapp and Ross (1986) have investigated the antibody response of swine to outer membrane components of *A. pleuropneumoniae: Infect. Immun.*, 54:751–760. The research particularly concerned the outer membrane proteins (OMPs), detecting antibodies to OMPs with apparent molecular weights of 16.5K, 29K, 38.5K, 43.5K, 45K, 49.5K, and 66.5K, but not to the major 42K OMP. To elucidate the nature of the antigens detected in immunoblots of sera, proteinase K treated lysates of OM were subjected to SDS-PAGE, and OM was also modified with sodium metaperiodate. By comparison of the SDS-PAGE profiles the OM protein components were differentiated from the saccharide components. It was suggested that the polysaccharide immunogens might be considered for subunit vaccines.

The convalescent sera used by Rapp and Ross were obtained from swine inoculated with live *H. pleuropneumoniae*. Rapp and Ross did not administer proteinase K-treated materials to pigs. The only use of proteinase K-treatment was for treatment of lysates of the organism prior to their use in vitro in SDS-PAGE or immunoblotting tests. Since immunogenicity is the ability of an antigen to induce an antibody response, reactions detected in vitro should not be interpreted as showing that an antigen is immunogenic. Antibodies which are detected in vitro do not necessarily have a role in protection against disease in the host animal. An immunogen may induce a multiplicity of antibody responses which have nothing to do with protection.

SUMMARY OF INVENTION

This invention is based on the discovery that protease lysates of outer membrane (P-OM) of *Actinobacillus pleuropneumoniae* cells can provide a protective action not obtainable with whole-cell bacterins or with OM bacterins.

Pleuropneumonia is an infection of swine respiratory mucosa primarily centered in the lungs. The protective threshold is provided by IgA antibodies produced in the respiratory mucosa. Heretofore, however, no vaccine has been shown to enhance protective IgA antibodies in the mucosa. It was surprising to discover that OM protease lysates administered parenterally can "sensitize" or "prime" respiratory mucosa for production of protective IgA. As demonstrated by challenge with virulent APP, IgA antibodies to the pathogen are produced in markedly greater quantities.

In addition, when two vaccine doses of P-OM are given, the pigs have higher specific IgG or IgA levels in airways compared to OM vaccinated pigs. Protective antibodies are thereby provided at the site of infection in advance of the infection. This can be expected to increase the effectiveness of the protection by acting together with the priming defense described above.

The foregoing results are surprising for several reasons. Parenteral administration is not usually considered to be an effective way to induce mucosal immunity. Moreover, protease digestion of a bacterin would be assumed to destroy or significantly reduce protective immunogenic effectiveness. The earlier published lysing treatment of OM was not for the purpose of preparing a substitute vaccine but rather to evaluate which components of OM (protein or carbohydrate) were primarily involved in the protection of OM vaccinated pigs, that is, the proteinase K treatment was intended to destroy the protein as an immunogenic factor while leaving the carbohydrate immunogens. It was therefore very surprising to discover that the proteinase K lysate was a better immunogen than undegraded OM bacterin.

DETAILED DESCRIPTION

Strains of any serotype of *A. pleuropneumoniae* (APP) can be used for preparing the vaccines of this invention. Because of its prevalence, strains of serotype 5 are preferred. The "capsule" is the loosely-associated, outermost component of young APP cells. As the cells grow older, a great deal of capsule materials may be dissociated from the bacterial cells. In addition to the inner membrane, APP cells, like other gram negative bacteria, contain an outer-membrane (OM) which consists of lipopolysaccharide (LPS) and the proteins referred to as outer-membrane proteins. The OM can be separated and recovered, as described in Rapp and Ross (1986), cited above. This reference also refers to proteinase K digestion of OM fractions.

APP cells may be grown in an appropriate bacteriological medium, the bacterial cells harvested by centrifugation, disrupted by sonication, and extracted with Sarkosyl to selectively solubilize the inner membrane. The OM together with the capsule can then be pelleted by ultra-centrifuging the extract. Subsequently, the OM is treated with proteinase K to produce the lysate for vaccine use. Although proteinase K is a preferred enzyme, other proteases can be employed. The function of the protease is to degrade the protein components by enzymatic digestion while leaving the native OM lipopolysaccharide. Capsule polysaccharides may also be present. Digestion of the OM proteins need not be carried out to the amino acid stage, but only to the point where the lysate is essentially free of proteins with molecular weight above 20,000. With proteinase K, proteins can be degraded to molecular weights below 10,000 while avoiding complete degradation to amino acids.

PREPARATION AND USE OF VACCINE

Aliquots (0.25 ml) of APP stock culture are inoculated into tubes containing 5 ml of brain heart infusion broth (BHI) supplemented with NAD (40 µg/ml) and incubated overnight at 37° C. Preferably, a serotype 5 strain is used. The seed cultures (10 ml) then are inoculated into 100 ml of BHI-NAD broth in 250-ml Erlenmeyer flasks and incubated at 37° C. and 200 rpm for 6 h in a shaking water bath. Bacterial cells are harvested by centrifugation at 14,500×g for 20 min at 4° C., suspended in 10 mM HEPES buffer (n-2-hydroxyethylpiperazine-N'-2'-ethanesulfonic acid, pH 7.4; 10 ml of HEPES/400 ml of culture), and stored at −70° C.

To prepare OM, frozen bacterial cell suspension is thawed and disrupted with a sonicator equipped with a water-jacketed cylinder at 50% maximum output. Cells are sonicated with three to four bursts, 15 sec. each, with a 5 min cooling period between each burst. Throughout the sonication, the cylinder which contains bacterial cell suspension is in an ice bath with continuous flow of water through the water-jacket. Intact cells and cell debris are removed by centrifugation at 4,340×g for 30 min at 4° C., and the total membrane fraction is pelleted by ultracentrifugation at 100,000×g for 60 min at 4° C. The pellet is resuspended in 10 mM HEPES mixed with an equal volume of 2% Sarkosyl (sodium N-lauroyl sarcosinate) and incubated at room temperature for 30 min to selectively remove the inner membrane. OM then is pelleted by ultracentrifugation at 100,000×g for 60 min at 4° C. OM is suspended in deionized water to a concentration of 0.5 to 2 mg of protein per ml and stored at −70° C. Capsule polysaccharides may also be present.

To prepare P-OM vaccine, the protein concentration in OM is adjusted to 500 µg/ml followed by the addition of proteinase K (PK). 1–3 mg PK per mg protein of OM can be used. The mixture is incubated in a water bath at 60° C. for 60 min, mixed with equal volume of incomplete Freund's adjuvant (IFA), and homogenized by withdrawing and expelling repeatedly with a syringe.

Dosage of vaccine based on protein content before lysis is from 250 µg up to 1000 µg. A presently preferred dose on the same basis is about 500 µg, and is administered in 2 ml. The vaccine is preferably used with an appropriate adjuvant, such as Al(OH)$_3$. The vaccine may be given either subcutaneously or intramuscularly. A total of 2 doses is preferably given, 2–3 weeks apart. With 2 or more doses protective antibodies will be present in the mucosa of the airways to assist the priming defense mechanism initiated by a single dose.

The vaccine of this invention is especially effective against serotype 5 when prepared from this serotype. However, it is expected that the vaccine will be effective against a broad range of serotype, including serotypes 1 to 12. Alternatively or additionally, the vaccine can be prepared from the specific serotype against which it is to be used.

EXPERIMENTAL STUDY I

Vaccination and Experimental Infection

Pigs (9- to 10-weeks old) from a herd known to be free of porcine respiratory pathogens including *Haemophilus ssp.* and *A. pleuropneumoniae* were vaccinated with two doses of outer membrane (OM) or modified OM emulsified (1:1) in IFA (Difco), three weeks apart. Each dose of vaccine contained the equivalent of 500 micrograms (µg) of protein. The modified OM was either a proteinase K lysate of OM (P-OM) prepared as previously described, or OM treated with periodate (PI-OM) as a comparison. In the case of P-OM and PI-OM, the dosage was based on the protein content before modification. Vaccines were administered subcutaneously on each side of the neck. Control pigs received only the buffer (10 mM HEPES containing 0.037% formalin and 0.01% merthiolate) which was emulsified in IFA. Two weeks after the second dose, pigs were challenged intra-nasally with APP and necropsied one week later. Results of two trials are shown below in Tables 1 and 2.

TABLE 1

Efficacy of outer membrane fraction (OM), proteinase K-treated OM (P-OM), and periodate-treated OM (PI-OM) from *A. pleuroneumoniae* for protection of swine from pneumonia (Trial 1)

| Treatment | No. Pigs Pneumonia/challenged | % Pneumonia (Mean ± S.D.) |
| --- | --- | --- |
| Control | 3/5 | 4.2 ± 5.6 |
| OM Vaccinated | 0/4 | 0 |
| P-OM Vaccinated | 0/4 | 0 |
| PI-OM Vaccinated | 2/4 | 2.5 ± 4.6 |

[a]Pigs were challenged intransally with approximately 7.5 × 10$^6$ CFU.
[b]% of pneumonia-total area of lung lesions/total area of lung × 100

TABLE 2

Efficacy of outer membrane fraction (OM), proteinase K-treated OM (P-OM), and periodate-treated OM (PI-OM) from *A. pleuropneumoniae* for protection of swine from pneumonia (Trial 2)

| Treatment | No. Pigs Pneumonia/challenged | % Pneumonia (Mean ± S.D.) |
| --- | --- | --- |
| Control | 4/6 | 10.3 ± 11.5 |
| OM Vaccinated | 4/6 | 4.6 ± 5.4 |
| P-OM Vaccinated | 1/6 | 0.3 ± 0.7 |
| PI-OM Vaccinated | 3/6 | 5.3 ± 8.9 |

*Pigs were challenged intransally with approximately 2.1 × 10 CFU
*b% pneumonia-total area of lung lesions/total area of lung × 100

By considering the data of Table 1 and Table 2 it can be seen that the P-OM vaccinated pigs were more effectively protected than the OM-vaccinated pigs or the PI-OM vaccinates. The unmodified outer membrane (OM) contained the lipopolysaccharide and protein components of the membrane. The protease K lysate (P-OM) contained essentially native lipopolysaccharides together with degraded protein polypeptides, polypeptides, or amino acids of molecular weights below 20,000. OM treated with sodium metaperiodate (PI-OM) contains degraded lipopolysaccharides and undegraded proteins.

Vaccination of Pigs With P-OM Which Primes the Pigs to Mucosal Immune Response In a third trial, groups of pigs were vaccinated with two doses of OM or P-OM subcutaneously 3 weeks apart as described earlier and challenged intranasally with APP 2 weeks after the second dose. Lung lavage was performed on the day of first vaccination, 10 days after the second vaccination, and on the day of necropsy (24 days after the second vaccination). Pigs were premedicated by injecting acepromazine (1.5 mg/Kg) and atropine (0.044 mg/Kg) subcutaneously. Thiamylal was then given to induce a general anesthesia. The epiglottis was reflected and an endotracheal tube was inserted intratracheally and inflated. A modified Foley catheter was then inserted intratracheally and inflated to isolate a lobar segment. Sterile phosphate-buffered saline containing gentomycin (0.05 mg/ml) was introduced through the catheter into the isolated segment. A volume of 20 ml was introduced before aspiration is attempted. Specific IgA levels in lung washings were measured using ELISA. The results are shown below in Table 3.

The data of Table 3 shows that pre-challenge levels of IgA in lung washings from the OM and P-OM vaccinated pigs were comparable. Further, somewhat higher levels as compared with the control are not statistically significant for either the OM or P-OM vaccinates. The post-challenge results are quite different. With the OM-vaccine, IgA level in the lung washings post-challenge was comparable to that of the control, whereas pigs vaccinated with P-OM showed an IgA level more than three times that of control or the OM vaccinates. This difference is very marked and is statistically significant. This data indicates that protease lysates of outer membrane protein can function to sensitize respiratory mucosa for an IgA response to APP infection.

In a subsequent trial, 3 groups of 6 pigs were vaccinated, challenged, and necropised as described. Lung lavage was conducted only on the day of necropsy. The results are shown below in Table 4.

A higher IgA immune response was again observed in pigs vaccinated with P-OM although the differences between P-OM and other groups were not as big as in the previous trial. Similar to the previous trial, no significant difference in percentage of pneumonia was seen among the groups. This is believed to be due to a very weak challenge, which was not comparable to field infection.

TABLE 3

Specific IgA antibody levels* to APP antigens (OD$_{490}$ ± SD) in lung washings from control, OM-vaccinated and P-OM vaccinated pigs

| Treatment | Pre-immune | Pre-challenge | Post-challenge | No. Pigs Pneumonia/Challenged | % of Pneumonia |
| --- | --- | --- | --- | --- | --- |
| Control** (n = 3) | 0.059 ± 0.031 | 0.061 ± 0.013 | 0.026 ± 0.232 | 1/3 | 4.6 ± 8.0 |
| OM (n = 6) | 0.077 ± 0.043 | 0.085 ± 0.047 | 0.190 ± 0.056 | 1/6 | 1.5 ± 3.6 |
| P-OM (n = 6) | 0.045 ± 0.019 | 0.074 ± 0.026 | 0.675 ± 0.331 | 1/6 | 1.6 ± 3.7 |

*measured by ELISA
**number of pigs

TABLE 4

Specific IgA antibody levels* to APP LPS (OD$_{405}$ ± SD) in lung washings from control, OM vaccinated, and P-OM vaccinated pigs

| Treatment | IgA Level | % of Pneumonia | No. Pigs Pneumonia/Challenged |
| --- | --- | --- | --- |
| Control (n = 6)** | 0.123 ± 0.078 | 1.6 ± 4.0 | 1/6 |
| OM (n = 6) | 0.184 ± 0.144 | 1.5 ± 3.7 | 1/6 |
| P-OM (n = 6) | 0.348 ± 0.184 | 1.7 ± 3.9 | 1/6 |

*Measured by ELISA
**Number of Pigs

EXPERIMENTAL STUDY II

Materials and Methods

Animals

Cross-bred (Yorkshire-Hampshire-Landrace) male and female pigs were obtained at 9 to 10 weeks of age from the Iowa State University Animal Resource Station herd. The herd was established by surgical procurement and is barrier maintained. It was free of known respiratory pathogens including *Actinobacillus spp*. Pigs were randomly allocated to treatment groups on the basis of sex and litter of origin and housed in isolation rooms. Feed consisting of a 16 percent protein swine grower ration without antibiotics or other growth promotents was provided ad libitum.

Bacterium

*A. pleuropneumoniae* ISU strained 200 (APP 200; serotype 5) was used throughout this experimentation. For preparing bacterial antigens, APP 200 were inoculated in brain heart infusion broth, Difco Laboratories, Detroit, Mich. (BHI) supplemented with NAD, Sigma Chemical Co., St. Louis, Mo. (40 µg/ml), incubated for 7 h in a shaking water bath and harvested by centrifugation, as described in Rapp et al., *Infect. Immun.;* 1986, 54:751–760. For use in induction of experimental infection, bacteria were grown in M96 mycoplasma broth for 6 h and diluted in BHI to the desired concentration (See Rapp et al., 1986, cited above).

Bacterial Antigens

An outer membrane-enriched fraction (OM) of APP was prepared, as described in Rapp, et al. *Infect. Immun.*, 1986, 52:414–420. Briefly, bacteria suspended in 10 mM HEPES buffer (pH 7.4) were sonicated and then centrifuged to remove intact cells and cell debris. The total membrane fraction was sedimented by ultracentrifugation, treated with 1% (wt./vol.) sodium N-lauroyl sarcosinate, Sigma Chemical Co., St. Louis, Mo. (Sarkosyl) to selectively solubilize the inner membrane and again ultracentrifuged to pellet OM. Protein concentration of OM was determined by the method of Markwell et al., *Anal. Biochem.*, 1978, 87:206–210 using bovine serum albumin as standard.

Proteinase K-treated OM (P-OM) was prepared by adding proteinase K (Sigma Chemical Co., St. Louis Mo.) to OM in 10 mM HEPES buffer (3 mg proteinase K to 1 mg protein of OM) and incubating at 60° C. for 60 min. In one experiment, P-OM was also prepared by treating 1 mg of protein in OM with 1 mg of proteinase K.

Vaccination and Experimental Infection

Two doses of OM or P-OM emulsified (1:1) in incomplete Freund's adjuvant (IFA) were administered subcutaneously to swine at three week intervals. Each dose of vaccine contained 500 µg of protein in 2 ml. Proteinase K-treated OM vaccine contained the product derived from the same concentration of OM. Control pigs received only the buffer (10 mM HEPES containing 0.037% Formalin and 0.01% merthiolate) which was emulsified in IFA. Two weeks after the second dose, pigs were challenged intranasally with approximately $5 \times 10^6$ CFU of APP in 5 ml BHI of broth. Pigs were necropsied one week after challenge. Pneumonic lesions on the ventral and dorsal surfaces of lungs were drawn proportionally on a lung sketch. The lungs were sliced in approximately 1 cm sections and examined for any gross lesions which were not evident on the surface. The proportion of lung was determined using a digital image analyzer.

In one experiment, only one dose of OM or P-OM emulsified in IFA was administered to pigs. Three weeks after the vaccination, pigs were challenged intranasally with approximately $4 \times 10^7$ CFU APP 200 in 5 ml and necropsied one week later.

Lung Lavage

Lung lavage in live pigs was conducted. The pigs were premedicated with acepromazine and atropine. Thiamylal was then given to induce general anesthesia. The epiglottis was reflected, an endotracheal tube was inserted intratracheally and the cuff was inflated. A modified Foley catheter was then inserted and the balloon was inflated to isolate a lobar segment. Twenty ml of sterile phosphate-buffered saline (PBS; pH 7.2) containing gentamycin (50 µg/ml) was infused through the catheter and immediately withdrawn again into a syringe. Harvested fluid was placed in a centrifuge tube which was kept in ice until centrifuged ($12,100 \times g$ at 4° C. for 10 min). The supernate was aliquoted and stored at $-20°$ C. until used. For necropsied pigs, lung lavage was conducted immediately after the lung was excised.

Antibody Response

Serum samples were collected before first vaccination and weekly thereafter. Lung wash samples were collected before the first vaccination, one week after the second vaccination, and one week after challenge. For animals receiving only one dose of vaccine, lung wash samples were collected before vaccination, three weeks after vaccination, and one week after challenge. Antibody response to APP or OM was measured by ELISA. Serum samples were diluted 1:200 in a buffer containing 0.05M Tris-HCl, 0.15M NaCl, 1 mM EDTA, 0.1% bovine serum albumin and 0.05% Tween 20 (TSEBT) while lung wash samples were used undiluted. To evaluate the isotype of antibody responses, peroxidase-labeled goat anti-swine IgG, IgA or IgM, Kirkegarrd & Perry Laboratories, Gaithersburg, Mo. (heavy chain-specific) diluted 1:1,000 in TSEBT buffer was used. For an unknown reason, nonspecific reactions occurred with lung wash samples using goat anti-swine IgM conjugate. Therefore, for measuring IgM levels in lung wash samples, mouse anti-swine IgM monoclonal antibody diluted 1:100 in TSEBT buffer was used followed by the addition of peroxidase-labeled rabbit anti-mouse immunoglobulin diluted 1:1,000 in TSEBT buffer. Optical density (OD) was determined at 405 nm with an ELISA reader.

Data Analysis

The paired t-test was used to analyze the differences in antibody response measured by ELISA. The statistically significant level was set at $p < 0.05$.

RESULTS

Antibody Response

From 2 weeks after the first vaccination, P-OM vaccinated pigs had higher anti-LPS IgG levels in serum than those of OM vaccinated pigs. However, during the same period of time, anti-OM IgG levels in sera of P-OM vaccinated pigs were equivalent to those of OM vaccinated animals. Specific IgA and IgM responses induced by vaccination with either P-OM or OM were not as strong as the corresponding IgG response. Prior to challenge, higher IgA and IgM levels with either APP or OM specificity were detected in sera from P-OM vaccinated pigs compared to pigs vaccinated with OM. However, in contrast to IgG response, both IgA and IgM responses in P-OM vaccinated pigs seemed to be short-lived.

The preferential augmentation of antibody response was also found in lower airways of pigs vaccinated with P-OM. In most cases, the immune responses detected in airways were similar to those in serum. However, one important difference is that higher anti-OM IgG levels were found in airways of P-OM vaccinated pigs compared to OM vaccinated pigs whereas no difference was found in sera between these two groups.

Serum antibody responses to APP, LPS and OM in pigs vaccinated with one dose of OM or P-OM were similar to those in pigs receiving two doses of vaccine during the first 3 weeks after vaccination. No statistically significant difference was detected in immune responses induced by vaccination with P-OM prepared at 1:1 and 3:1 proteinase:OM ratios. Nevertheless, anti-LPS IgG levels were substantially higher in pigs vaccinated with P-OM prepared with higher concentration of proteinase K at two or three weeks after vaccination.

Higher IgG levels, although not significant, were detected in airways of pigs vaccinated with one dose of P-OM vaccines compared to pigs vaccinated with one dose of OM. However, in contrast to the findings in pigs receiving two doses of vaccine, no distinctly higher levels of specific IgA or IgM antibodies were detected in airway washings from pigs vaccinated with one dose of P-OM vaccines compared to OM vaccinated pigs or even to control animals in some cases. One noteworthy difference between the immune response detected in serum and in airways of pigs vaccinated with single dose of P-OM is that the exposure to APP challenge increased IgA and IgM levels in airway washings, while serum IgA and IgM levels continuously declined.

Experimental Infection

Pigs vaccinated with two doses of OM or P-OM were protected from challenge with APP (Table 5). Twenty-four hours after challenge, two control pigs were very depressed and dyspneic and were given antibiotic treatment. Despite the treatment, one pig died. Vaccination with P-OM vaccine and OM vaccine conferred comparable protection. In contrast, in the experiment in which pigs received only one dose of vaccines, P-OM vaccine improved protection over that provided by OM vaccine (Table 6).

TABLE 5

Protection of swine from pleuropneumonia by vaccination with two doses of OM or P-OM vaccine.

| Treatment | No. Pigs Died/ Challenged (%) | No. Pigs Pneumonia/ Challenged (%) | % Lung w/ Lesions[a] (Mean ± S.D.) |
|---|---|---|---|
| Control | 1/5 (20) | 3/5 (60) | 14.6 ± 8.7 |
| OM | 0/5 (0) | 1/5 (20) | 0.7 ± 0.7 |
| P-OM | 0/5 (0) | 2/5 (40) | 0.8 ± 0.5 |

[a]% lung lesions = area of lung lesions/total area of lung × 100.

TABLE 6

Protection of swine from pleuropneumonia by vaccination with one dose of OM or P-OM vaccine.

| Treatment | No. Pigs Pneumonia/ Challenged (%) | % Lung w/ Lesions[a] (Mean ± SEM) |
|---|---|---|
| Control | 3/4 (75) | 3.5 ± 3.0 |
| OM | 4/5 (80) | 9.5 ± 6.5 |
| P-OM (3:1)[b] | 2/5 (40) | 1.4 ± 0.6 |

TABLE 6-continued

Protection of swine from pleuropneumonia by vaccination with one dose of OM or P-OM vaccine.

| Treatment | No. Pigs Pneumonia/ Challenged (%) | % Lung w/ Lesions[a] (Mean ± SEM) |
|---|---|---|
| P-OM (1:1)[c] | 1/4 (25) | 1.0 ± 1.0 |

[a]% lung with lesions = area of lung lesions/total area of lung × 100.
[b]Treated with 3 mg of proteinase K per mg of protein.
[c]Treated with 1 mg of proteinase K per mg of protein.

The present invention is believed to be of general applicability to pneumonia-type mucosal infections of domestic animals; including *Pasteurella multocida* in swine; *P. haemolytica* in cattle, and *P. haemolytica* in sheep. By preparing lysates of the outer membranes of those bacteria, as described in the foregoing specification, useful vaccines for sensitizing respiratory mucosa of the swine, cattle or sheep against these infections can be produced.

We claim:

1. The method of increasing the resistance of swine to infection by serotypes of *Actinobacillus (Haemophilus) pleuropneumoniae*, comprising prior to infection parenterally administering to the swine at least one dose of a respiratory mucosa sensitizing-effective amount of a protease lysate of the outer membrane (OM) of *Actinobacillus (Haemophilus) pleuropneumoniae* cells, said lysate containing native OM lipopolysaccharide together with an antigenic protease digest of OM protein essentially free of protein of molecular weight above 20,000.

2. The method of claim 1 in which said lysate is formed by digesting said outer membrane with proteinase K.

3. The method of claim 1 in which said cell membranes are obtained from *A. pleuropneumoniae* of serotype 5.

4. The method of claims 1, 2 or 3 in which said lysate is administered subcutaneously.

5. The method of claims 1, 2 or 3 in which said lysate is administered intramuscularly.

6. The method of claims 1, 2 or 3 in which two doses of said lysate are successively administered.

7. The method of sensitizing respiratory mucosa of swine for production of IgA antibodies following infection with *Actinobacillus (Haemophilus) pleuropneumoniae*, comprising prior to infection parenterally administering to the swine at least one dose of a proteinase K lysate of outer membrane (OM) from serotype 5 *A. pleuropneumoniae* cells, said lysate containing native OM lipopolysaccharide and a protease digest of OM protein essentially free of protein of molecular weight above 20,000 and said dose containing an amount of lysate corresponding to at least 250 micrograms (μg) of OM protein.

8. The method of claim 7 in which two doses of the lysate are successively administered.

* * * * *

UNITED STATES PATENT AND TRADEMARK OFFICE
CERTIFICATE OF CORRECTION

PATENT NO. : 5,332,572

DATED : July 26, 1994

INVENTOR(S) : Richard F. Ross et al

It is certified that error appears in the above-identified patent and that said Letters Patent is hereby corrected as shown below:

On the title page, second inventor "Yu-Wei Chaing" should read --Yu-Wei Chiang--.

Signed and Sealed this

Twenty-fifth Day of July, 199

Attest:

BRUCE LEHMAN

*Attesting Officer*     *Commissioner of Patents and Trademarks*